(12) United States Patent
Litvay

(10) Patent No.: US 8,283,516 B2
(45) Date of Patent: Oct. 9, 2012

(54) ABSORBENT PRODUCT WITH LOW DRYNESS INDEX

(76) Inventor: John D. Litvay, Al Hamra Free Zone (AE)

( * ) Notice: Subject to any disclaimer, the term of this patent is extended or adjusted under 35 U.S.C. 154(b) by 379 days.

(21) Appl. No.: 12/416,464

(22) Filed: Apr. 1, 2009

(65) Prior Publication Data
US 2010/0256584 A1   Oct. 7, 2010

(51) Int. Cl.
*A61F 13/15* (2006.01)
*A61F 13/20* (2006.01)

(52) U.S. Cl. ............... 604/367; 604/385.101; 604/383

(58) Field of Classification Search ............ 604/383, 604/385.101, 367–369; 428/131
See application file for complete search history.

(56) References Cited

U.S. PATENT DOCUMENTS

| | | | |
|---|---|---|---|
| 6,623,464 B2 * | 9/2003 | Bewick-Sonntag et al. | 604/385.03 |
| 6,632,209 B1 | 10/2003 | Chmielewski | |
| 6,703,846 B2 | 3/2004 | Delzer et al. | |
| 2004/0133180 A1 | 7/2004 | Mori et al. | |
| 2005/0267429 A1 * | 12/2005 | Cohen | 604/378 |
| 2006/0020250 A1 | 1/2006 | Chester et al. | |
| 2006/0040579 A1 | 2/2006 | Sheldon et al. | |
| 2006/0069367 A1 | 3/2006 | Waksmundzki et al. | |
| 2006/0167424 A1 | 7/2006 | Chang et al. | |
| 2008/0065038 A1 | 3/2008 | Sugiyama et al. | |

FOREIGN PATENT DOCUMENTS

| | | |
|---|---|---|
| WO | WO 00/59432 | 10/2000 |
| WO | WO 2008/018921 | 2/2008 |

* cited by examiner

*Primary Examiner* — Melanie Hand
(74) *Attorney, Agent, or Firm* — Pillsbury Winthrop Shaw Pittman LLP

(57) ABSTRACT

The embodiments provide an absorbent garment, such as a disposable diaper, incontinent pad, sanitary napkin, and the like, that has an absorbent core that provides for a long term dryness profile. The dryness profile reflects real world long term usage of absorbent products. Such new absorbent garments can be constructed with absorbent cores containing synthetic fibers and super absorbent particulates.

17 Claims, 3 Drawing Sheets

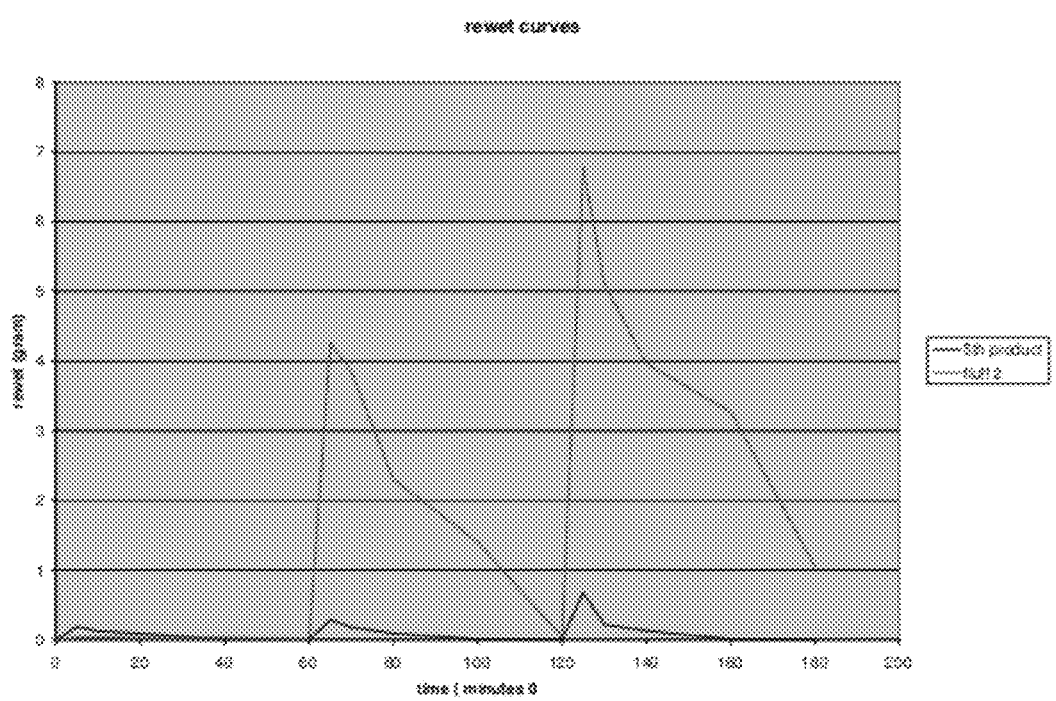

ABSORBENT PRODUCT WITH LOW DRYNESS INDEX

BACKGROUND

1. Field of the Invention

Embodiments of the invention include absorbent products having improved dryness. Specifically, the invention pertains to absorbent products having a dryness index within the range between of from about 0 to about 50 gm/180 min.

2. Description of Related Art

Absorbent products, such as baby diapers have a 90 to 95% market penetration in the United States and Europe. The levels of market penetration in some of the emerging market countries such as China and India, however, is less than 5%. Part of the reason for this low level of penetration is the relative high cost of these products in those markets.

Manufacturers of absorbent products in the emerging market countries face an enormous challenge in trying to find ways to produce low cost effective products. The cost of raw materials comprise up to seventy to eighty percent of the cost to manufacture such products. Production of functional absorbent products usually requires a minimum amount of conventional materials, including absorbent components, and leakage-resistant materials. Reducing the amount of material used beyond these minimums can greatly diminish the product's functionality.

Absorbent products such as baby diapers, feminine hygiene pads and adult incontinent products typically are made of several different types of materials. These products usually include a permeable non-woven top sheet, an impermeable back sheet and an absorbent core positioned between the top sheet and the back sheet. The absorbent core typically consists of wood fluff and a water-absorbing polymer, which most commonly is prepared from monomers of acrylic acid. This water-absorbing polymer, referred to as super absorbent polymer (SAP), can constitute anywhere from about 20% up to 50% of the material cost of the product. In addition, availability of SAP fluctuates, and in those times in which there is a shortage of SAP, the costs can be much higher. Wood-based fluff can account for an additional 10-20% of the material cost of the product.

Conventional absorbent garments having wood-based fluff cores tend to release moisture under pressure over the long term. Baby diapers in particular and some adult incontinent diapers may be worn for long periods of time (2 to 8 hours). Wood-based fluff over that period of time can release moisture through pressure or evaporation. Wood-based fluff does not actually absorb the liquid like SAP. The long term comfort of the wearer therefore is compromised due to the release of this moisture.

Accordingly, there is a need in the art for a cost effective absorbent garment having improved long term dryness profile that will provide for a much more comfortable and hygienic product.

The description herein of certain advantages and disadvantages of known elements of absorbent garments, methods, and systems is not intended to limit the scope of the present invention to either their inclusion or exclusion. Indeed, certain embodiments may include one or more known elements without suffering from the disadvantages described herein.

SUMMARY

Various features of the embodiments provide an absorbent garment, such as disposable diapers, adult incontinent pads, sanitary napkins, and the like, that include an absorbent core that provides an improved long term dryness profile. One embodiment provides a synthetic absorbent core that includes SAP having a high Centrifuge Retention Capacity (CRC) having an improved long term dryness profile. The dryness profile reflects real world long term usage of absorbent products. The embodiments provide a new and improved absorbent product having a dryness index within the range from about 0 to about 50 gm/180 min. Such new absorbent garments are constructed with absorbent cores containing synthetic fibers and super absorbent particulates.

The above and other features and advantages of the embodiments will become apparent to those having ordinary skill in the art from a review of the following detailed description of the preferred embodiments.

DETAILED DESCRIPTION OF DRAWINGS

Various features and embodiments of the preferred embodiments described herein will be described with reference to the following non-limiting drawings, in which:

FIG. 3 is a graph illustrating the rewet curves produced from three insults of over time for a wood-based fluff containing conventional diaper (fluff 2) and a filament tow pulpless diaper of the embodiments ($5^{th}$ product).

DETAILED DESCRIPTION OF INVENTION

Figure 1:
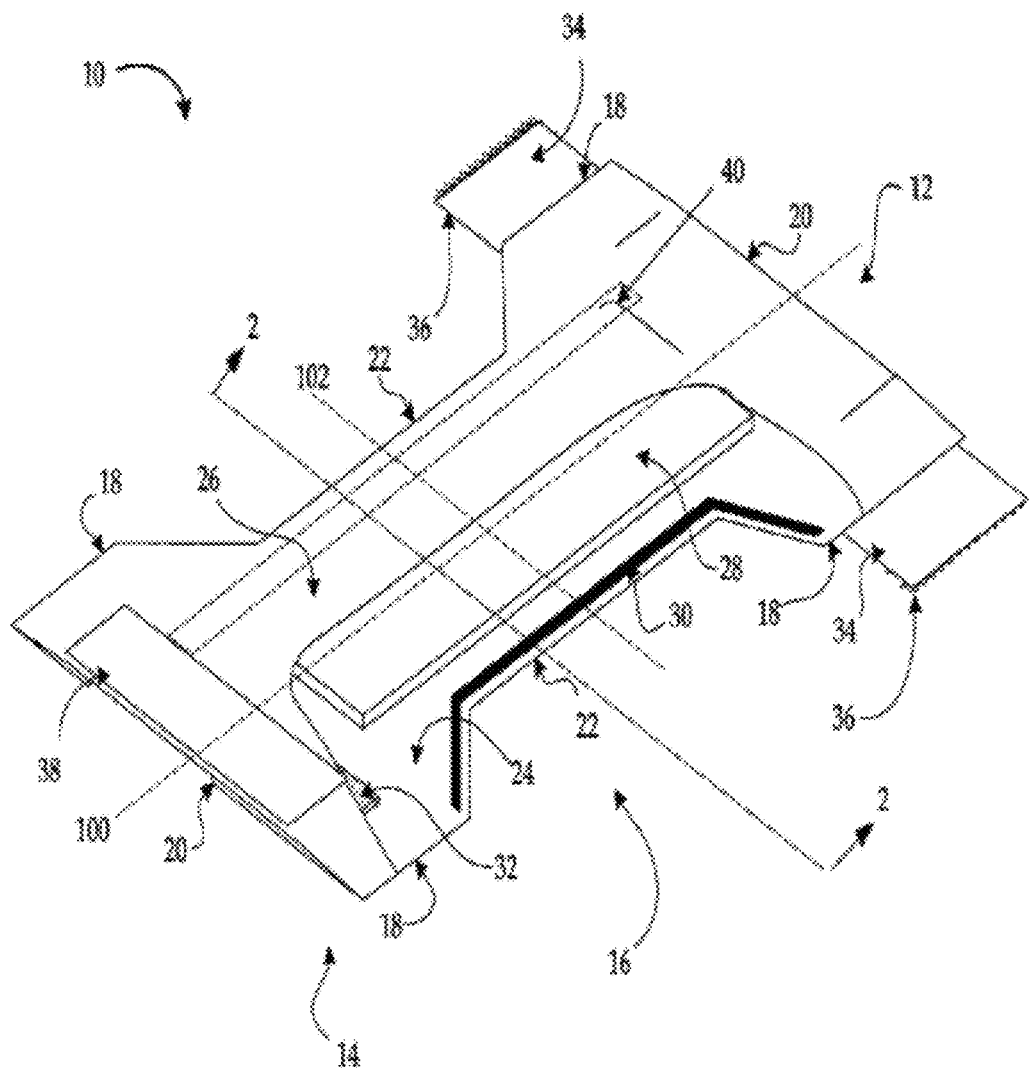
FIG. 1 illustrates a top view of a diaper having an absorbent synthetic core.

Embodiments of the invention relate to absorbent garments with improved long term (greater than one hour) dryness profiles, when compared to conventional absorbent garments made with wood-based fluff and SAP. Throughout this description, the expression "absorbent garments" or "absorbent products" or "absorbent articles" denote disposable diapers, incontinent pads, sanitary napkins, adult incontinence garments, absorbent surgical gowns, absorbent surgical sheets or tissue, and the like. In preferred embodiments, the absorbent core of the preferred absorbent articles comprises synthetic fibers and super absorbent polymer.

While not intending on being bound by any theory of operation, the inventor discovered that absorbent products that include synthetic absorbent cores comprised of at least SAP having a high Centrifuge Retention Capacity (CRC) have a superior long term dryness profile when compared to absorbent products having conventional cores that include the more costly low CRC SAP in wood-based fluff.

Throughout this description, the expressions "upper layer," "lower layer," "above" and "below," which refer to the various components included in the absorbent composite and absorbent core embodiments (including the layers surrounding the absorbent core units) are used merely to describe the spatial relationship between the respective components. The upper layer or component "above" the other component(s) need not always remain vertically above the core or component(s), and the lower layer or component "below" the other component(s) need not always remain vertically below the core or component(s). Indeed, embodiments include various configurations in which the core may be folded in such a manner that the upper layer ultimately becomes the vertically highest and vertically lowest layer at the same time. Other configurations are contemplated within the context of the present embodiments.

The term "component" can refer, but is not limited to, designated selected regions, such as edges, corners, sides or the like; structural members, such as elastic strips, absorbent pads, stretchable layers or panels, layers of material, a transfer layer, a fluid handling layer, or the like; or a graphic.

Throughout this description, the term "disposed" or "positioned," and the expressions "disposed on," "disposed in," "disposed between" and variations thereof (e.g., a description of the article being "disposed" is interposed between the words "disposed" and "on") are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a substrate that is placed with or near the element, formed or applied within a layer of the element or another substrate, or other variations or combinations thereof.

Throughout this description, the expressions "top sheet" and "back sheet" denote the relationship of these materials or layers with respect to the absorbent core. It is understood that additional layers may be present between the absorbent core and the top sheet and back sheet, and that additional layers and other materials may be present on the side opposite the absorbent core from either the top sheet or the back sheet.

Throughout this description, the expression "tow fibers" relates in general to any continuous fiber. Tow fibers typically are used in the manufacture of staple fibers, and preferably are comprised of synthetic thermoplastic polymers. Usually, numerous filaments are produced by melt extrusion of the molten polymer through a multi-orifice spinneret during manufacture of staple fibers from synthetic thermoplastic polymers in order that reasonably high productivity may be achieved. The groups of filaments from a plurality of spinnerets typically are combined into a tow which is then subjected to a drawing operation to impart the desired physical properties to the filaments comprising the tow. Tow as used in the context of the present embodiments also encompasses modified tow fibers that have been either surface or internally modified (chemically or otherwise) to improve various desired properties of the fibers (e.g., wicking, etc.), and tow fibers include those made from recycled thermoplastic polymers.

Throughout this description, the expression "super absorbent polymer" ("SAP") or "super absorbent material" refers to any polymeric material that is capable of absorbing large quantities of fluid by forming a hydrated gel. Super absorbent polymers are well-known to those skilled in the art as substantially water-insoluble, absorbent polymeric compositions that are capable of absorbing large amounts of fluid (e.g., 0.9% solution of NaCl in water, or blood) in relation to their weight and forming a hydrogel upon such absorption. Super absorbent polymers also can retain significant amounts of water under moderate pressures. Super absorbent polymers generally fall into three classes, namely, starch graft copolymers, cross-linked carboxymethylcelluose derivatives, and modified hydrophilic polyacrylates. Examples of such absorbent polymers are hydrolyzed starch-acrylonitrile graft copolymer a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-cross-linking polyacrylic acid, a cross-linked polyacrylate salt, carboxylated cellulose, and a neutralized cross-linked isobutylene-maleic anhydride copolymer.

Throughout this description the expression "dryness profile" denotes the ability of the absorbent garment to maintain dryness over time, after insulted with bodily fluids or solids. Specifically, "dryness profile" denotes absorbent garments having a "dryness index" within the range of from about 0 to about 50 gm/180 min. Preferably, the dryness index is within the range of from about 5 to about 35 gm/180 min, and most preferably, the dryness index is within the range of from about 10 to about 25 gm/180 min.

Throughout this description, "dryness index" denotes the value determined by first measuring the rewet values of an absorbent garment in various time intervals (5, 10, 20, 40 and 60 minutes), in which the rewet values are measured for 3 insults of 50 mls each of 1.0% saline solution. Each insult produces a rewet curve, and the area under each curve can be determined by integrating the curve. The dryness index is the sum of the areas of the three curves (or the sum of the integrals of the three curves). The dryness index can be calculated in accordance with the following equation $$\text{Dryness index} = \sum_{n=1}^{3} \int (rewetcurve)n$$

Embodiments of the invention also include those in which the absorbent garment includes a "synthetic absorbent core," and has a dryness index of less than about 200 gsm, preferably less than about 150 gsm, and most preferably less than about 100 gsm. As used throughout this description, the expression "synthetic absorbent core" denotes an absorbent core comprised of SAP and synthetic fibers, (preferably tow fibers) and substantially no wood-based fluff pulp. Substantially no wood-based fluff pulp means less than 2% by weight fluff, preferably less than about 0.5% by weight, and most preferably, no fluff pulp.

The embodiments now will be described with reference to the attached drawings illustrating preferred embodiments. Some of the features that appear in more than one figure do not necessarily have the same reference number in each Figure.

FIG. 1 is a partially cut away depiction of an exemplary embodiment of an absorbent garment 10 (preferably a disposable absorbent garment). The embodiment shown in FIG. 1 is an infant's diaper. This depiction, however, is not intended to limit the preferred embodiments, and a person having ordinary skill in the art will appreciate that the preferred embodiments cover other types of absorbent articles. For simplicity, the preferred embodiments will be described with reference to an infant's diaper. The garment 10 of FIG. 1 is depicted in a generally flattened position, with the body-facing side facing down, and with the various elastic components depicted in their relaxed condition with the effects of the elastics removed for clarity (when relaxed, the elastics typically cause the surrounding material to gather or "shirr"). In the flattened position, the garment 10 may have a generally hourglass shaped structure, but it may also have any other shape suitable for the given application, such as a rectangular shape, a trapezoidal shape, a "T" shape, and the like.

As used herein, the longitudinal axis 100 of the garment is the dimension of the garment corresponding to the front-to-rear dimension of the user, and the lateral (or transverse) axis 102 of the garment is the dimension corresponding to the side-to-side dimension of the user. The longitudinal axis 100 and the transverse axis 102 make up the longitudinal plane of the garment.

In use, the embodiments comprise a garment 10 having a pant-like configuration with a waist-encircling region and a crotch region. The waist-encircling region may comprise a first waist region 12, disposed adjacent to, for example, the back waist region of a wearer's body, and a second waist region 14, disposed adjacent to, for example, the front waist region of a wearer's body, when the garment is worn. The first and second waist regions 12, 14, may correspond to the front and back of the wearer's body, respectively, depending on whether garment 10 is attached in front of or behind the subject wearer. The first and second waist regions may be joined together at or near their lateral edges 18, causing the longitudinally distal edges 20 of the garment 10 to form the perimeter of a waist opening. A crotch region 16 extends between the first and second waist regions, 12, 14, and the crotch edges 22 form the perimeter of a pair of leg openings, when the garment 10 is placed on a subject wearer.

The garment preferably comprises a top sheet 24, and a back sheet 26. When the garment 10 is being worn, the top sheet 24 faces the wearer's body, and the back sheet 26 faces away from the wearer. An absorbent core 28 preferably is positioned between at least a portion of the top sheet 24 and the back sheet 26.

A feature of an embodiment may further comprise various additional features. One or more pairs of elastic gathers 30 (leg elastics) may extend adjacent the crotch edges 22. The garment 10 also may comprise one or more waste containment systems, such as inboard standing leg gathers 40, which preferably extend form the second waist region 14 to the first waist region 12 along opposite sides of longitudinal center line 100 (only one standing leg gather system 40 is shown in FIG. 1 for purposes of clarity). One or both of the first and second waist regions 12, 14 may also be equipped with strips of waist elastic material 32, such as elastic waist foam or other elastically extensible material, which help contract the garment around the wearer's waist, providing improved fit and leakage prevention. In addition, the ear portions of the garment, e.g., those portions immediately adjacent lateral edges 18 and extending to crotch edges 22, can be comprised entirely or only partially of elastically extensible material (not shown).

The absorbent garment 10 also preferably includes fastening elements to enable attachment of the first waist region 12 to second waist region 14. Fastening elements preferably include a pair of tabs 34 that extend laterally away from opposite lateral edges 18 of the first waist region 12 of the garment 10. The tabs 34 may comprise in whole or in part an elastically extensible material (not shown), and may be designed to stretch around a wearer's waist to provide improved fit, comfort, and leakage protection. Such tabs 34 may be used in conjunction with, or in lieu of, waist elastic material 32, such as foam, or other elastically extensible materials.

At least one fastening mechanism 36 (collectively referred to as "fastener 36") is attached to each tab 34 for attaching the tab to the second waist region 14, thereby providing the garment 10 with a pant-like shape, and enabling garment 10 to be fixed or otherwise fitted on the wearer. The fasteners 36 may attach to one or more target devices 38 located in the second waist region 14. For example, in one embodiment, the fastening mechanism is a hook and loop fastener in which one fastening element is a hook portion, and a corresponding target device is a loop portion of the hook and loop fastener, or the target device may be the backsheet itself. In another embodiment, the fastening mechanism is a tape fastener system in which one fastening element is an adhesive tape, and a corresponding target device is a tape receiving surface. Other fastening systems may be used in the embodiments, so long as they are capable of fastening the garment 10 about the wearer.

Although not shown in the drawings, the absorbent garment 10 also may include grips attached along the distal edges of each tab 34 to enable a caregiver to pull the grips, and not on the ends of the tabs 34, around the wearer and over the target devices 38 to thereby secure the fasteners 36 to the one or more target devices 38.

The various parts of the garment 10 can be attached to one another or associated with one another to form a structure that preferably maintains its shape during the useful life of the garment 10. As used herein, the terms "attached", "joined", "associated", and similar terms encompass configurations in which a first part is directly joined to a second part by affixing the first part directly to the second part, by indirectly joining the first part to the second part through intermediate members, by fixing the relative positions of various parts by capturing parts between other parts, or by integrally forming the first and second parts. Persons having ordinary skill in the art will appreciate that various methods or combinations of methods may be used to securely join, attach, or otherwise associate the respective parts of the garment 10 to one another.

The top sheet 24 and back sheet 26 may be constructed from a wide variety of materials known in the art. The embodiments are not intended to be limited to any specific materials for these components. The back sheet 26 preferably is made from any suitable pliable liquid-impervious material known in the art. Typical back sheet materials include films of polyethylene, polypropylene, polyester, nylon, and polyvinyl chloride and blends of these materials. For example, the back sheet can be made of a polyethylene film having a thickness in the range of 0.02-0.04 mm. The back sheet 26 may be pigmented with, for example, titanium dioxide, to provide the garment 10 with a pleasing color or to render the back sheet 26 opaque enough that exudates being contained by the garment 10 are not visible from outside the garment. In addition, the back sheet 26 may be formed in such a manner that it is opaque, for example, by using various inert components in the polymeric film and then biaxially stretching the film. Other back sheet materials will be readily apparent to those skilled in the art. The back sheet 26 preferably has sufficient liquid imperviousness to prevent any leakage of fluids. The required level of liquid imperviousness may vary between different locations on the garment 10. The back sheet 26 may be covered with a fibrous, non woven fabric such as is disclosed, for example, in U.S. Pat. No. 4,646,362 issued to Heran et al., the disclosure of which is hereby incorporated by reference in its entirety.

The top sheet 24 preferably is moisture-pervious, or fluid-permeable, thereby allowing fluids and other body exudates to flow there-through. The moisture-pervious top sheet 24 can be comprised of any suitable relatively liquid-pervious material known in the art that permits passage of liquids. Non-woven liner sheet materials are exemplary because such materials readily allow the passage of liquids to the underlying absorbent core 28. Examples of suitable liner sheet material include non-woven spun bond or carded webs of polypropylene, polyethylene, nylon, polyester, and blends of these materials.

The top sheet 24 and back sheet 26 can be shaped and sized according to the requirements of each of the various types of absorbent garments, or to accommodate various user-sizes. In an embodiment in which the garment 10 is a diaper or an adult incontinence brief, the combination of top sheet 24 and back sheet 26, may have an hourglass shape, as seen in FIG. 1, or may have a rectangular, trapezoidal, "T" shape, or other shape.

The underlying structure beneath the top sheet 24 may include, depending on the diaper construction, various combinations of elements, but in each embodiment, it is contemplated that the absorbent garment preferably will include an absorbent core 28 comprising synthetic fibers and SAP. An additional layer 29 may be positioned between the top sheet 24 and absorbent core 28, and/or other additional layer(s) 29 may be positioned between these layers, or between absorbent core 28 and back sheet 26. The additional layer(s) 29 may include a fluid transfer layer, a fluid handling layer, a storage layer, a wicking layer, a fluid distribution layer, and any other layer(s) known to those having ordinary skill in the art.

Although the absorbent core 28 depicted in FIG. 1 has a substantially rectangular cross-sectional and plan view shape, other shapes may be used, such as a "T" shape or an hourglass shape. The shape of the absorbent core 28 may be selected to provide the greatest absorbency with a limited amount of material. The absorbent core may be associated with the top sheet 24, back sheet 26, or any other suitable part of the garment 10 by any method known in the art, in order to fix the absorbent core 28 in place. Persons of ordinary skill in the art are capable of designing and wrapping a suitable absorbent core 28 of the embodiments, using the guidelines provided herein.

Figure 2:
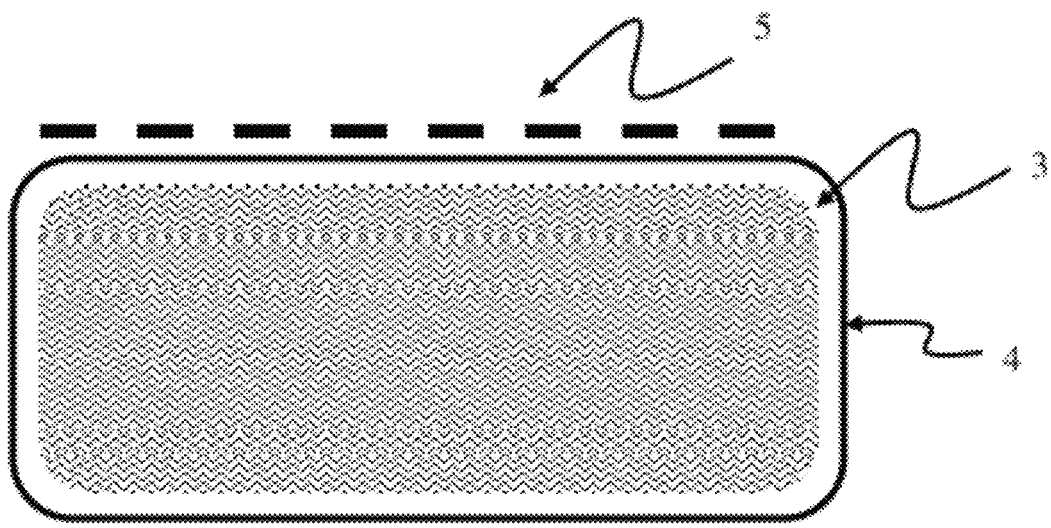
FIG. 2 illustrates a cross-sectional view of an absorbent core showing the synthetic fibers.

FIG. 2 shows a cut away cross-section of absorbent core 1. FIG. 2 illustrates a synthetic fiber matrix 3, a wrap material 4 and an acquisition layer 5. The absorbent core 1 can be comprised of any synthetic material known in the art and SAP. Preferably, the synthetic fiber matrix 3 includes tow and SAP. "Tow" or tow fibers" as they are used herein, include synthetic materials such as polyolefins, rayon, polycarbonates and cellulose acetate. Polyolefins include polypropylene and polyethylene.

Absorbent core 1 can be prepared by methods known in the art. For example, the feeding system disclosed in U.S. Pat. No. 6,923,926, which is incorporated herein by reference in its entirety, can be used to prepare the synthetic fiber matrix that includes the tow material and SAP. It also is understood that the manufacture of the absorbent core can be done off-line and separate from the manufacturing of the remainder of the absorbent garment components. It is possible, for example, to have one absorbent core-forming unit supply several diaper manufacturing machines.

Combinations of certain types of SAP applied in certain patterns within a synthetic core may result in an absorbent core that provides absorbent garments with an excellent long-term dryness profile. To establish which combinations are most effective, the present inventor developed a protocol to determine the dryness index so that absorbent articles prepared in accordance with the preferred embodiments could be compared to conventional products with respect to long-term dryness. The dryness index can be determined by measuring the rewet values of an absorbent garment in various time intervals (5, 10, 20, 40 and 60 minutes), in which the time intervals were measured for 3 insults of 50 mls each of 1.0% saline solution. Each of the three resultant rewet curves then are integrated, and dryness index represents the sum of the integral values (or area under the rewet curves) for the three curves. The dryness index can be calculated in accordance with the following equation:

$$\text{Dryness index} = \sum_{n=1}^{3} \int (rewetcurve)n$$

The preferred embodiments of the invention now will be described with reference to the following non-limiting example.

EXAMPLES

The present invention preferably utilizes the following 1$^{st}$ insult procedure to measure the rewet values over each time interval. It is preferred to use the following experimental protocol:
 diaper was laid open absorbent core and transfer layer facing up;
 50 mls of a 1.0% saline solution was applied to the center of the transfer layer;
 at 5, 10, 20, 40 and 60 minute time intervals blotter papers (90 mm×140 mm) were applied to the insult area under a 4800 g weight (90 mm×140 mm) for 30 seconds; and
 the blotter papers were then removed and weighed.

Various products prepared in accordance with the preferred embodiments of the present invention were compared to the following 4 commercially available diapers prepared using wood-based fluff pulp absorbent cores. The first commercial product (Fluff #1) was a Lido branded product (manufactured by Fine Hygienic, United Arab Emirates), which had approximately 6 grams of SAP and 30 grams of fluff pulp, and the non-woven acquisition layer (basis weight approximately 35 grams/m$^2$ (gsm)), which did not run the full length of the core. The second commercial product (Fluff #2) was a Pampers product (from P&G Saudia Arabia) having about 10 grams of SAP and 15 grams of fluff pulp, and the non-woven acquisition layer (basis weight of about 40 gsm) also did not run the full length of the core. The third commercial product (Fluff #3) was a Huggies branded product (from Kimberly Clark, Saudi Arabia) having about 10 grams of SAP and 15 grams of fluff pulp, in which the acquisition layer had a basis weight of approximately 50 gsm and did not run the full length of the core. The fourth commercial product (Fluff #4) was a Bambi branded product (NAPCO, Saudi Arabia) having about 8 grams of SAP and 15 grams of fluff pulp, and the non-woven acquisition layer (basis weight about 40 gsm) also did not run the full length of the core.

The various products made in accordance with the preferred embodiments of the invention that are utilized in the examples described herein are described in more detail as follows.

The first absorbent garment ("1$^{st}$ Test Product") of the present invention comprised an acquisition layer comprised of an apertured polyolefin film having a basis weight of about 36 gsm, purchased from Tredegar, Richmond, Va. The acquisition layer did not run the complete length of the absorbent core. The absorbent core included about 13.5 grams of SAP (HySorb purchased from BASF, Germany) having a Centrifuge Retention Capacity (CRC) of about 29.

The second absorbent garment ("2$^{nd}$ Test Product") of the present invention comprised an acquisition layer comprised of a non-woven polyolefin film having a basis weight of about 45 gsm (purchased from Pantex International, Italy), which ran the full length of the absorbent core. The absorbent core included about 13.5 grams of SAP (HySorb purchased from BASF, Germany) having a CRC of about 29.

The third absorbent garment ("3$^{rd}$ Test Product") of the present invention comprised an acquisition layer comprised of an apertured polyolefin film having a basis weight of 36 gsm (purchased from Tredegar, Richmond, Va.), which ran the full length of the absorbent core. The absorbent core included about 13.5 grams of SAP (HySorb purchased from BASF, Germany) having a CRC of about 29.

The fourth absorbent garment ("4$^{th}$ Test Product") of the present invention comprised an acquisition layer comprised of an apertured polyolefin film having a basis weight of about 36 gsm (purchased from Tredegar, Richmond, Va.) which did not run the complete length of the absorbent core. The absorbent core included about 14 grams of SAP (HySorb purchased from BASF, Germany) having a CRC of about 29, and was wrapped with a phillic non-woven material having a basis weight of about 12.5 gsm.

The Fifth absorbent garment ("5$^{th}$ Test Product") of the present invention comprised an acquisition layer comprised of an apertured polyolefin film with a basis weight of about 29 gsm (purchased from Tredegar, Richmond, Va.) which did not run the complete length of the absorbent core. The absorbent core included about 14 grams of SAP (purchased from Kolon Chemical Company, South Korea) having a CRC of about 41.

The sixth absorbent garment ("6th Test Product") of the present invention comprised an acquisition layer comprised of an apertured polyolefin film with a basis weight of about 29 gsm (purchased from Tredegar, Richmond, Va.) which did not run the complete length of the absorbent core. The absorbent core included about 10.5 grams of SAP (purchased from Kolon Chemical Company, South Korea) having a CRC of about 41.

The single insult results are compiled in Table 1 below.

These values then can be plotted to reflect the 1$^{st}$ insult rewet values over time, and the area under the 1$^{st}$ insult rewet curve can be calculated by integrating the area under the rewet curves. This will represent the first area value that can be used in calculating the dryness index.

The present invention preferably utilizes the following 2$^{nd}$ insult procedure to measure the rewet values for each insult over each time interval. It is preferred to use the following experimental protocol:
the diaper was laid open absorbent core and transfer layer facing up;
50 mls of 1.0% saline solution was applied to the center of the transfer layer;
after 60 minutes a second 50 mls of 1.0% saline solution was applied to the center of the transfer layer;
at 5, 10, 20, 40 and 60 minute time intervals blotter papers (90 mm×140 mm) were applied to the insult area under a 4800 g weight (90 mm×140 mm) for 30 seconds; and
the blotter papers were then removed and weighed.

Various embodiments of product of the present invention were compared to 4 commercially available diapers with fluff matrix absorbent cores. The second insult results are compiled in Table 2 below.

TABLE 2

| Minutes | 1$^{st}$ Test Product | 2$^{nd}$ Test Product | 3$^{rd}$ Test Product | 4$^{th}$ Test Product | 5$^{th}$ Test Product | 6$^{th}$ Test Product | Fluff #1 | Fluff #2 | Fluff #3 | Fluff #4 |
|---|---|---|---|---|---|---|---|---|---|---|
| 5 | 0.56 | 3.49 | 0.83 | .75 | 0.33 | 0.29 | 4.26 | 4.26 | 1.53 | 3.23 |
| 10 | 0.33 | 2.07 | 0.57 | .40 | 0.29 | 0.18 | 2.53 | 3.85 | 0.56 | 2.30 |
| 20 | 0.13 | 0.73 | 0.15 | .34 | 0.10 | 0.09 | 2.17 | 2.29 | 0.10 | 1.45 |
| 40 | 0.02 | 0.10 | 0.24 | .19 | 0.02 | 0.01 | 0.85 | 1.40 | 0.1 | 0.78 |
| 60 | 0.02 | 0.05 | 0.24 | .04 | 0.02 | 0.01 | 0.54 | 0.03 | 0.07 | 0.96 |

These values then can be plotted to reflect the 2$^{nd}$ insult rewet values over time, and the area under the 2$^{nd}$ insult rewet curve can be calculated by integrating the area under the rewet curves. This will represent the second area value that can be used in calculating the dryness index.

The present invention preferably utilizes the following 3$^{rd}$ insult procedure to measure the rewet values over each time interval. It is preferred to use the following experimental protocol:
the diaper was laid open absorbent core and transfer layer facing up;
50 mls of 1.0% saline solution was applied to the center of the transfer layer;
after 60 minutes a second 50 mls of 1.0% saline solution was applied to the center of the transfer layer;
after 60 minutes a third 50 mls of 1.0% saline solution was applied to the center of the transfer layer;
at 5, 10, 20, 40 and 60 minute time intervals blotter papers (90 mm×140 mm) were applied to the insult area under a 4800 g weight (90 mm×140 mm) for 30 seconds; and
the blotter papers were then removed and weighed.

TABLE 1

| Minutes | 1$^{st}$ Test Product | 2$^{nd}$ Test Product | 3$^{rd}$ Test Product | 4$^{th}$ Test Product | 5$^{th}$ Test Product | 6$^{th}$ Test Product | Fluff #1 | Fluff #2 | Fluff #3 | Fluff #4 |
|---|---|---|---|---|---|---|---|---|---|---|
| 5 | 0.47 | 2.23 | 1.50 | .23 | 0.29 | 0.19 | 0.08 | 0.045 | 0.11 | 0.13 |
| 10 | 0.27 | 1.77 | 1.45 | .27 | 0.19 | 0.12 | 0.07 | 0.04 | 0.07 | 0.1 |
| 20 | 0.11 | 0.94 | 0.26 | .13 | 0.13 | 0.09 | 0.05 | 0.03 | 0.08 | 0.11 |
| 40 | 0.05 | 0.15 | 0.51 | .05 | 0.03 | 0.01 | 0.03 | 0.03 | 0.09 | 0.06 |
| 60 | 0.03 | 0.04 | 0.09 | .03 | 0.04 | 0.01 | 0.02 | 0.02 | 0.08 | 0.06 |

Various products of the present invention were compared to 4 commercially available diapers with fluff matrix absorbent cores. The 3rd insult results are compiled in Table 3 below.

TABLE 3

| Minutes | $1^{st}$ Test Product | $2^{nd}$ Test Product | $3^{rd}$ Test Product | $4^{th}$ Test Product | $5^{th}$ Test Product | $6^{th}$ Test Product | Fluff #1 | Fluff #2 | Fluff #3 | Fluff #4 |
|---|---|---|---|---|---|---|---|---|---|---|
| 5  | 0.82 | 6.33 | 2.48 | 1.23 | 0.83 | 0.68 | 5.41 | 6.78 | 2.84 | 4.45 |
| 10 | 0.64 | 4.06 | 0.98 | .98  | 0.46 | 0.22 | 5.69 | 5.11 | 1.6  | 4.23 |
| 20 | 0.21 | 1.55 | 0.49 | .41  | 0.20 | 0.13 | 4.24 | 3.96 | 0.57 | 3.16 |
| 40 | 0.04 | 1.41 | 0.25 | .20  | 0.06 | 0.01 | 2.40 | 3.26 | 0.06 | 1.84 |
| 60 | 0.01 | 0.42 | 0.20 | .01  | 0.04 | 0.01 | 2.73 | 1.04 | 0.34 | 1.01 |

These values then can be plotted to reflect the $3^{rd}$ insult rewet values over time, and the area under the $3^{rd}$ insult rewet curve can be calculated by integrating the area under the rewet curves. This will represent the third area value that can be used in calculating the dryness index.

The dryness index can be calculated by adding up the area under each rewet curve ($1^{st}$ insult, $2^{nd}$ insult, and $3^{rd}$ insult rewet curve). The area under each rewet curve can be determined by taking the integral over the 60 minute period of the measured rewet values at each time interval. The present inventor established the dryness index as a mechanism to more accurately reflect the dryness profile of an absorbent garment than simply by relying on rewet value data.

There are a variety of methods that are useful for determining the rewet values for absorbent products. These rewet values usually are taken at discrete time points within a discrete insult level, similar to the values found in Tables 1-3 above. The rewet value is purportedly a way of assessing the dryness of the absorbent article under actual field or in use conditions. With diapers the babies skin health is related to dryness and is a major performance need. Besides leakage, dryness is the next most important attribute for a diaper.

Most of these methods, however, fail to accurately or adequately mimic real world in-use conditions because of the protocols used (short time spans). For example, it is well know that an average insult for a baby in a large size diaper is approximately 50-75 mls. It also is well know that the average time between insults is approximately 45-60 minutes, and that diapers are normally worn for 3-4 hours during the daytime, and 8-12 hours during the nighttime. Finally, it is known that SAP, unlike wood pulp, will continue to absorb urine for extremely long periods of time. As the industry shifts from diapers using high levels of wood-based fluff to high levels of SAP, the absorption time-to-dryness relationship also is shifting. Thus, the present inventor perceived a need to develop a test method and analysis that more realistically mimics real-world in the field results. That testing protocol is described in more detail below, and in the examples.

The test methodology uses three 50 ml insults of 1% saline over a three hour interval (one insult per 60 minute time interval). Plotting the actual rewet values at various times during this 3 hour interval produces curves similar to those seen in FIG. 3. These curves represent the actual moisture exposure that the baby experiences over time. Analysis of these curves by integrating these curves then provides the actual dose that affects the baby and its skin. The resultant integrals of each insult and the sum of the integrals of the three insults are show in Table 4 and are The Dryness Index for that product.

Table 4 provides the results achieved in accordance with the preferred examples. As shown in Table 4, each rewet curve ($1^{st}$ insult, $2^{nd}$ insult, and $3^{rd}$ insult rewet curves) was integrated to provide a total $1^{st}$ insult dryness (gsm), a total $2^{nd}$ insult dryness (gsm), and a total $3^{rd}$ insult dryness (gsm), respectively. The respective dryness values then are added to provide the dryness index for that particular absorbent article. The values are shown below in Table 4.

TABLE 4

|  | 1st product | 2nd product | 3rd product | 4th product | 5th product | 6th product | fluff 1 | fluff 2 | fluff 3 | fluff 4 |
|---|---|---|---|---|---|---|---|---|---|---|
| 1st insult gm/60 min  | 6.3  | 36.1  | 28.7 | 4.31  | 3.6  | 1.9  | 5.5   | 3.1   | 11.0 | 9.4   |
| 2nd insult gm/60 min  | 7.8  | 37.6  | 16.5 | 11.1  | 6.3  | 5.5  | 85.5  | 105.9 | 14.1 | 72.9  |
| 3rd insult gm/60 min  | 13.3 | 117.6 | 28.2 | 17.0  | 10.2 | 5.5  | 189.0 | 189.8 | 30.6 | 135.7 |
| Index gm/180 min      | 27.5 | 191.4 | 73.4 | 32.44 | 20.1 | 12.9 | 280.0 | 298.8 | 55.7 | 218.0 |

Analysis of Table 4 shows that test products 1, 4, 5, and 6 are superior to all other conventional products tested. The conventional products were selected to provide a reasonable cross-section of known products on the market today. The $3^{rd}$ test product and Fluff product #3 form a second tier of dryness performance products, while the $2^{nd}$ test product and fluff products 1, 2 and 4 form a third level of dryness performance that is far inferior to test products 1, 4, 5, and 6. One difference between the test products of the invention and the fluff products, however, is that the test products did not include any wood-based fluff pulp to make up the absorbent core. Accordingly, these products are much less expensive to manufacture, and are thinner.

Embodiments of the invention therefore also include those in which the absorbent garment includes a synthetic absorbent core, and has a dryness index of less than about 200 gm/180 min, preferably less than about 150 gm/180 min, and most preferably less than about 100 gm/180 min. The use of the Dryness Index thus the selection of material and processing combinations to achieve superior performance products under a more realistic and accurate methodology to assess diaper dryness.

For example, a person having ordinary skill in the art can prepare the absorbent garment such that it includes a fluid acquisition layer that preferably does not run the entire length of the absorbent core. A diaper designer also can select SAP having a high CRC, as well as use synthetic materials instead of wood-based fluff pulp to comprise the core.

The preferred embodiments of the invention provide an absorbent garment having an improved dryness profile over time, as reflected by a dryness index within the range of from about 0 to about 50 gm/180 min. Preferably, the dryness index is within the range of from about 5 to about 35 gm/180 min, and most preferably, the dryness index is within the range of from about 10 to about 25 gm/180 min.

It is envisaged that embodiments of the present invention will include varying the number of insults, insult amount or time interval to more accurately mimic alternative sized diapers, adult products or even baby diaper night time use (insult levels approaching 200-300 mls over 8 hours).

Using the description of the various test products above, the results shown in Table 4 can be compared amongst the test products to assess the effect certain parameters have on the dryness index. Table 5 below provides the various materials used for certain components of the test diaper products.

TABLE 5

| Component | 1st product | 2nd product | 3rd product | 4th product | 5th product | 6th product |
|---|---|---|---|---|---|---|
| Transfer layer | Film 36* | Non-Woven | Film 36 | Film 36 | Film 29 | Film 29 |
| Coverage of TL | Half | Half | Full | Half | Half | Half |
| SAP | BASF 13.5** | BASF 13.5 | BASF 13.5 | BASF 13.5 | Kolon 14 | Kolon 10.5 |
| Core Wrap | Tissue | Tissue | Tissue | Non-Woven | Tissue | Tissue |

*the number after Film denotes basis weight
**the number after the SAP denotes the amount of SAP used Using tables 4 and 5 above, comparing test product 1 with test product 2 will show the effect of an apertured film acquisition layer (test 1), when compared to a non-woven film acquisition layer (test 2). The results reveal that use of an apertured film for the acquisition layer decreases the dryness index. Comparing test product 1 with test product 3 reveals that a full length transfer layer provides an inferior dryness index than a half length transfer layer. This is counterintuitive. While not intending on being bound by any theory of operation, the inventor believes that moisture may be trapped by the transfer layer/core wrap when the transfer layer is the full length of the core.

Comparing test product 1 with test product 4 will show the effect the type of core wrapping on the dryness index. Test product 1 utilizes a tissue core wrapping material, whereas test product 4 utilizes a non-woven. The results shown in Table 4 reveal that there is not much difference between the two test products. Use of a non-woven material may be preferred, however, for recycling purposes. Test product 1 also can be compared with test product 5 to show the effect of the type of SAP used. The results shown in Table 4, in which test product 5 had a superior dryness index, are somewhat unexpected because it was generally known that fluff-pulp-containing diapers that used Kolon SAP had high rewet values, when compared with similar diapers using other SAP products. Thus, the fact that Kolon SAP provided a superior dryness index to a BASF SAP was unexpected. While not intending on being bound by any theory of operation, it is believed that some of the preferred parameters of the present invention (i.e., no fluff in core, etc.) render the effects of the type and amount of SAP used less pronounced.

Comparing test product 1 with test product 6 compares a lower CRC SAP at a higher amount (BASF (CRC 29) at 13.5 grams) with a higher CRC SAP at a reduced amount (Kolon (CRC 41) at 10.5 grams). The results reveal that a higher CRC SAP, even at much lower amounts, provides a superior dryness index. Test product 1 should have a capacity of about 391.5 grams (CRC 29×13.5 grams), whereas test product 6 should have a capacity of about 430 grams (CRC 41×10.5). Thus, the invention enables the use of lower amounts of a higher CRC SAP, which should provide significant savings in costs.

Finally, test product 5 can be compared with test product 6 to show the effects of the amount of high CRC SAP used (test product 5 uses 13.5 grams, whereas test product 6 uses only 10.5 grams). The results show that less SAP actually provided a superior product in terms of dryness index, although the dryness index values are relatively similar. This comparison shows that a capacity of 430 grams (CRC of 41×10.5 grams) is more than adequate to absorb three 50 gram insults.

The aforementioned embodiments and examples are for explanatory purposes and are in no way meant to be limiting. Various other configurations are possible within the spirit of the invention. The scope of the invention intends to cover all such embodiments within the boundaries limited only by the appended claims.

I claim:

1. An absorbent product comprising:
   a. a liquid permeable top sheet;
   b. an absorbent core comprising:
      i. synthetic fibers;
      ii. super absorbent particulate having a centrifuge retention capacity (CRC) within the range of from about 29 to about 41; and
   c. a back sheet
   wherein the absorbent core has a dryness index in the range of between about 0 to about 50 gm/180 min, and
   wherein the dryness index is determined by first measuring the rewet values of an absorbent garment at various time intervals, in which the rewet values are measured for 3 insults of 50 mls each of 1.0% saline solution, each insult producing a rewet curve, and the area under each curve is determined by integrating the curve to measure the rewet, and then calculating the dryness index as the sum of the areas of the three curves, in accordance with the following equation:

$$\text{Dryness index} = \sum_{n=1}^{3} \int (rewetcurve)n.$$

2. The absorbent product of claim 1, wherein the synthetic fibers are selected form the group consisting of rayon, polypropylene, polyethylene, polyethylene terephthalate (PET), and mixtures thereof.

3. The absorbent product of claim 1, wherein the absorbent product further comprises an acquisition layer positioned between the top sheet and the absorbent core.

4. The absorbent product of claim 3, wherein the acquisition layer comprises an apertured polyolefin film.

5. The absorbent product of claim 3, wherein the acquisition layer has a basis weight in the range of from about 20 to about 40 g/m² (gsm).

6. The absorbent product of claim 3, wherein the acquisition layer has a basis weight of about 29 gsm.

7. The absorbent product of claim 4, wherein the acquisition layer has a basis weight within the range of from about 20 to about 40 gsm.

8. The absorbent product of claim 4, wherein the acquisition layer has a basis weight of about 29.

9. The absorbent product of claim 1, wherein the dryness index is within the range of from about 5 to about 35 gm/180 min.

10. The absorbent product of claim 1, wherein the absorbent core is wrapped in a non-woven material.

11. An absorbent product comprising:
    a. a liquid permeable top sheet;
    b. an absorbent core comprising an absorbent material comprising:
        i. synthetic fibers;
        ii. super absorbent particulate having a centrifuge retention capacity (CRC) within the range of from about 29 to about 41; and
        iii. substantially no wood-based fluff pulp
    c. a back sheet
    wherein the absorbent core has a dryness index of less than about 200 gm/180 min, and
    wherein the dryness index is determined by first measuring the rewet values of an absorbent garment at various time intervals, in which the rewet values are measured for 3 insults of 50 mls each of 1.0% saline solution, each insult producing a rewet curve, and the area under each curve is determined by integrating the curve to measure the rewet, and then calculating the dryness index as the sum of the areas of the three curves, in accordance with the following equation:

$$\text{Dryness index} = \sum_{n=1}^{3} \int (rewetcurve)n.$$

12. The absorbent product of claim 11, wherein the absorbent core has a dryness index of less than about 100 gm/180 min.

13. The absorbent product of claim 11, wherein the synthetic fibers are selected form the group consisting of rayon, polypropylene, polyethylene, polyethylene terephthalate (PET), and mixtures thereof.

14. The absorbent product of claim 11, wherein the absorbent product further comprises an acquisition layer positioned between the top sheet and the absorbent core.

15. The absorbent product of claim 14, wherein the acquisition layer comprises an apertured polyolefin film.

16. The absorbent product of claim 14, wherein the acquisition layer has a basis weight in the range of from about 20 to about 40 g/m² (gsm).

17. The absorbent product of claim 15, wherein the acquisition layer has a basis weight within the range of from about 20 to about 40 gsm.

* * * * *